Sept. 3, 1974 SING LING LEE Plant Pat. 3,608
CHRYSANTHEMUM PLANT
Filed April 13, 1973
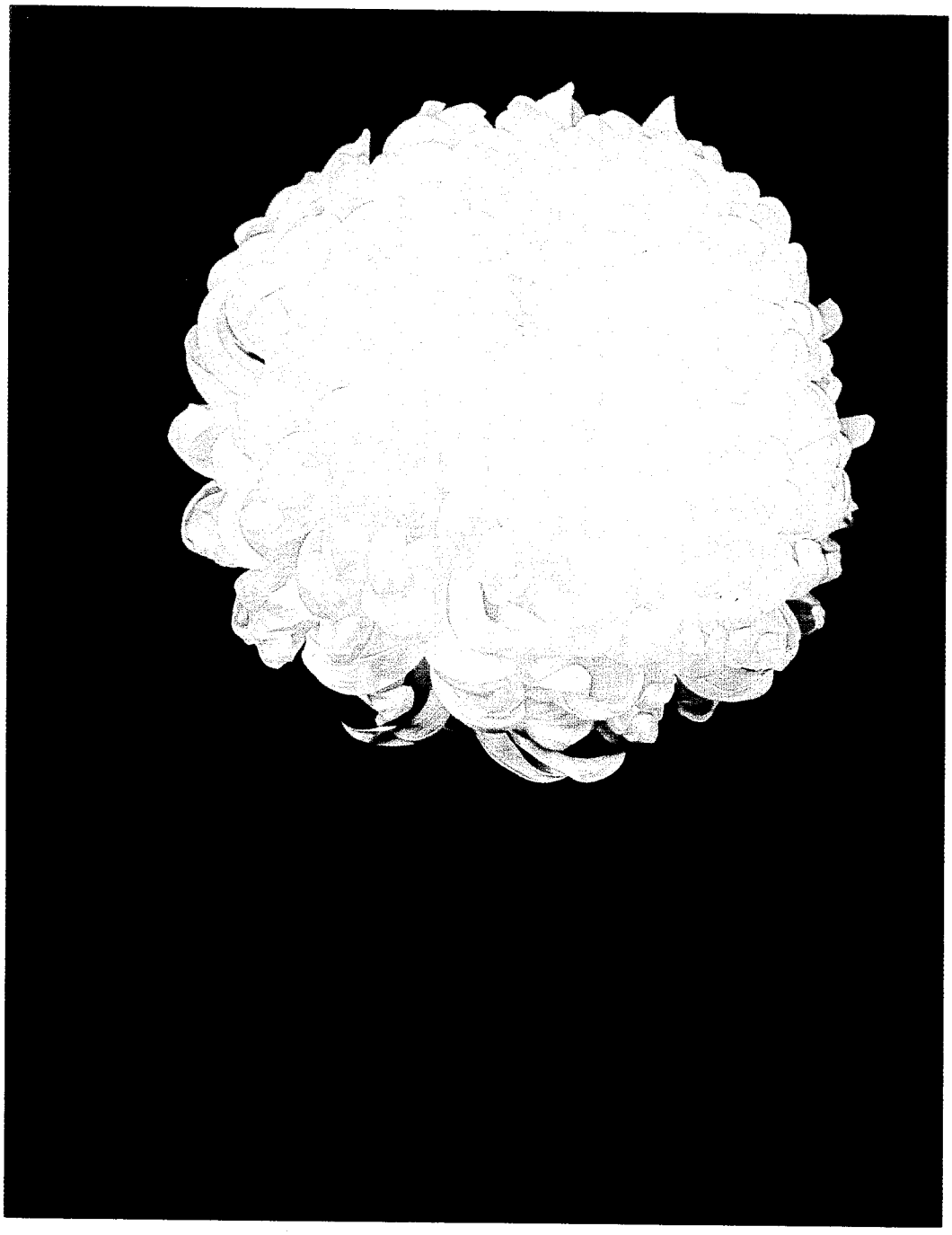

United States Patent Office

Plant Pat. 3,608

Patented Sept. 3, 1974

3,608

CHRYSANTHEMUM PLANT

Sing Ling Lee, 206 Sleeper Ave., Mountain View, Calif. 94040

Filed Apr. 13, 1973, Ser. No. 350,910

Int. Cl. A01h *5/00*

U.S. Cl. Plt.—78 1 Claim

The present invention comprises a new and distinct cultivar of chrysanthemum plant known by the varietal name Yellow Jumbo Albatross. The new cultivar is a sport of the cultivar known in the United States as Jumbo Albatross, disclosed in my issued U.S. Plant Pat. 3,249.

The new cultivar is similar in many respects to Jumbo Albatross, having the same characteristics of:

1. A similar recommended flowering period.
2. The same foliage shape, size and color.
3. Equal vigor.
4. Approximate flower size.
5. Similar petal form, in that the petals are tubular and closed at the base and flare to a rounded deep keel which tapers to a blunt tip. Most petals have a finger-like or pointed protuberance(s) which arise on the side of the petals near the opening of the tubed base. This unique trait of both the new cultivar and the parent Jumbo Albatross, when grown at a minimum temperature of 60° F. or above for initiation and development, has never been observed on the cultivar Albatross, and is only rarely seen on the cultivars Improved Albatross and #2 Yellow Albatross. Similar tubular petals have occasionally been observed on Improved Yellow Albatross, but the protuberances which arise on the side of the petals near the opening of the tube on Yellow Jumbo Albatross and Jumbo Albatross rarely develop on Improved Yellow Albatross at 60° F. minimum temperatures, or above.

The new cultivar is distinguished from Jumbo Albatross by its yellow flower color.

The new cultivar was discovered as a flowering plant in a greenhouse in Mt. View, Calif., and when asexually reproduced by cuttings at Mt. View, Calif., has been found to retain its distinctive characteristics through successive propagations.

The new cultivar when grown in the vicinity of Mt. View, Calif. has a response period of approximately 8 weeks, and the following detailed description is based on observations made of the new cultivar in a greenhouse in Mt. View, Calif. The response time, blooming period, color, and total vigor may vary significantly with varying environmental conditions such as temperature, day length, and light intensity. Suggested flowering in the northern and western United States is from April through May and November 1 through November 15. Suggested flowering in coastal California, is from April through November.

The accompanying photographic drawing shows the unique color characteristic of the new cultivar, the color being as nearly true as possible with color illustrations of this type.

In the description which follows, color references are made to the Munsell Color Book, 1963 edition, and color comparisons are made with the cultivar Jumbo Albatross. Where a single value or description appears only for the new cultivar, the same value or description applies to the parent cultivar as well.

Botanical classification: *Chrysanthemum morifolium*

| | Yellow Jumbo Albatross | Jumbo Albatross |
|---|---|---|
| **Bloom:** | | |
| Size | 5½" | |
| Fully expanded | 6" | |
| Borne | Singly on disbudded plant | |
| Stems | Strong | |
| Form | Incurve | |
| Permanence | 10 days | |
| Color: | | |
| Center of flower | Medium yellow, 7.5Y8.8/7.2 | Pale yellow, 7.5Y9/4. |
| Base of petals | Yellow-green, 2.8GY8.8/9.2 | Pale yellow, 7.5Y9/4. |
| Inside of petals | Deep yellow 7.4Y8.7/9.6, to light yellow, 1.5GY9.1/4.0 | Pale ivory, 5Y9/1. |
| Reverse of petals | Yellow 0.6GY9.0/7.8 to ivory, 2.1GY9.1/2.0 | Pale ivory, 5Y9/1. |
| Tonality from a distance | Medium yellow | White (ivory). |
| Discoloration | Light yellow, 1.5GY9.1/4.0 | Pale ivory, 5Y9/1. |
| **Petals:** | | |
| Texture | Smooth | |
| Appearance and form | Petals tubular and closed at the base, flaring to a rounded deep keel which tapers to a blunt tip. Most petals have a finger-like or pointed protuberance(s) which arise on the side of the petals near the opening of the tubed base. This petal form also appears on the parent Jumbo Albatross, and clearly distinguishes both the new and parent cultivars from currently available selections of Yoder Brothers, Inc., Barberton, Ohio, from the Albatross group, including Albatross, #2 Yellow Albatross, Improved Albatross and Improved Yellow Albatross. The unique petal form, when grown at a minimum temperature of 60° F. or above for initiation and development, has never been observed on the cultivar Albatross, and is only rarely seen on the cultivars Improved Albatross and #2 Yellow Albatross. Although similar tubular petals have occasionally been observed on Improved Yellow Albatross, the protuberances which arise on the side of the petals near the opening of the tube on the new cultivar and the parent cultivar Jumbo Albatross rarely develop on Improved Yellow Albatross at 60° F. minimum temperatures, or above. | |
| Arrangement | Composite, whorled on a single receptacle | |
| Persistence | Resist shatter | |
| Fragrance | Typical chrysanthemum | |
| **Reproductive organs:** | | |
| Stamen, anthers | None to 5 | |
| Pollen | None | |
| Arrangement | Clustered in center of flower, if present | |
| Styles | Present both ray and disc florets | |
| Length | Short | |
| Ovaries | At the base of petal attached to receptacle | |
| **Plant:** | | |
| Form | Herbaceous | |
| Growth | Upright | |
| Height | Approximately 42"–44" when grown as a single stem crop, given 3–4 long day weeks and a total crop time of 11–12 weeks as required in spring through fall flowering at Mt. View, Calif. | |
| Spread | None | |

TABLE—Continued

| | Yellow Jumbo Albatross | Jumbo Albatross |
|---|---|---|
| Foliage: | | |
| Top side | Dark green, 7.5GY2/4 | |
| Size | 5¾″ long, 3¼″ wide | |
| Quantity | Numerous | |
| Shape | Spatulate lobed | |
| Texture | Smooth | |
| Ribs and veins | Prominent | |
| Edge | Moderately indented | |
| Serration | Very slight | |
| Under side | Green, 7.5GY4/4 | |
| Stipules | Prominent but small | |

I claim:

1. A new and distinct cultivar of chrysanthemum characterized particularly as to its uniqueness when compared to the parent cultivar Jumbo Albatross by its yellow flower color.

No references cited.

ROBERT E. BAGWILL, Primary Examiner